(12) United States Patent
Linz et al.

(10) Patent No.: US 7,601,863 B2
(45) Date of Patent: Oct. 13, 2009

(54) USE OF PPAR AGONISTS FOR THE TREATMENT OF CONGESTIVE HEART FAILURE

(75) Inventors: Wolfgang Linz, Mainz (DE); Stefan Schaefer, Liederbach (DE); Eugen Falk, Frankfurt (DE); Hans-Ludwig Schaefer, Hochheim (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/762,799

(22) Filed: Jun. 14, 2007

(65) Prior Publication Data

US 2008/0039512 A1    Feb. 14, 2008

(30) Foreign Application Priority Data

Dec. 17, 2004   (EP)   ................... 04029946

(51) Int. Cl.
*C07C 69/017*    (2006.01)
*C07C 69/00*     (2006.01)
*C07C 63/04*     (2006.01)

(52) U.S. Cl. .................. 560/103; 424/569; 514/374
(58) Field of Classification Search .................. 514/374
See application file for complete search history.

(56) References Cited

U.S. PATENT DOCUMENTS 6,624,185 B2    9/2003   Glombik 6,989,462 B2    1/2006   Maier

FOREIGN PATENT DOCUMENTS

| WO | WO 00/64888   | 11/2000 |
|----|---------------|---------|
| WO | WO 2004/103997 | 2/2004  |
| WO | WO 2004/082621 | 9/2004  |

*Primary Examiner*—Ardin Marschel
*Assistant Examiner*—Meghan Finn
(74) *Attorney, Agent, or Firm*—Ronald G. Ort

(57) ABSTRACT

The invention describes the use of PPAR agonists of the formulae (I) or (II)

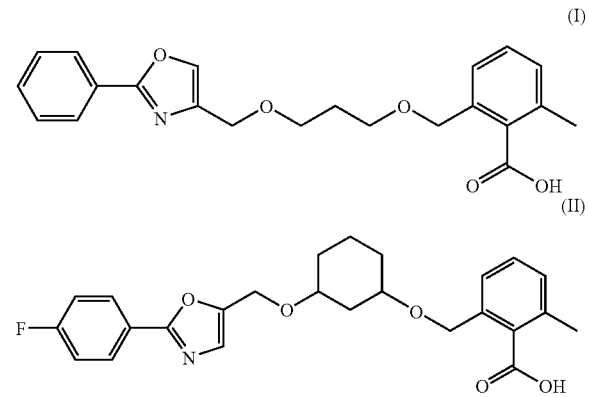

for the treatment of congestive heart failure (CHF).

1 Claim, No Drawings

USE OF PPAR AGONISTS FOR THE TREATMENT OF CONGESTIVE HEART FAILURE

Congestive heart failure is a devastating disease where there is ineffective pumping of the heart leading to an accumulation of fluids in the lungs. Typical symptoms include shortness of breath, difficulty breathing when lying flat and swelling of legs and ankles. Said progressive impairment of physical fitness can ultimately lead to death. There are a number of causes for heart failure but the most frequent are myocardial infarction (about 60 percent of all cases), chronic hypertension (about 25%), genetic disposition (10%) and cardiomyopathy, or a combination of these factors.

In patients, the severity of CHF is categorized according to the clinical symptoms, based on a classification developed by the New York Heart Association (NYHA). The patients physical fitness determines the classification into NYHA I (no symptoms), NYHA II (symptoms during moderate exertion), NYHA III (symptoms during mild exertion), or NYHA IV (symptoms at rest).

Current treatment of CHF that delay the progression of CHF prolong survival considerably. Nevertheless, at any given NYHA stage, overall mortality has remained high, averaging 15 percent per year in recent large scale trials performed in patients with mainly NYHA II or III. A common aspect of all currently approved CHF medications with a proven mortality benefit (e.g., diuretics, ACE inhibitors, β-blockers) is their blood pressure lowering effect. Combination therapy is often not possible because in many patients blood pressure will decrease too much. As a consequence, alternative therapeutic strategies, targeting novel mechanisms of action, are urgently needed for the further advancement of medical therapy of CHF.

The peroxisome proliferator activator receptors (PPARs) represent a class of nuclear hormone receptors, two of which (PPARα and PPARγ) are expressed in many tissues, including the myocardium and the vessels. Activation of the PPARs leads to expression of a variety of genes and, subsequently, production of proteins. The PPARγ activators (e.g., rosiglitazone) have been approved for the treatment of type 2 diabetes mellitus, based on their efficacy in improving insulin sensitivity and delaying the progression of insulin resistance into overt diabetes (Malinowski and Bolesta Clin. Therapeutics (2000), 22, 1151-1168; Leff and Reed, Curr. Med. Chem. Immunology, Endocrine & Metabolic Agents (2002), 2, 33-47). In addition some PPARα activators, the fibrates, are in clinical use because of their ability to reduce blood cholesterol levels (Sacks-F M, Am. J. Cardiol. (2001), 88(12A), 14N-18N). Novel PPARα activators, which are structurally different from the fibrates and more potent, are in clinical development for lipid disorders and diabetes mellitus (Inoue and Katayama, Current Drug Targets: Cardiovascular & Haematological Disorders (2004), 4, 35-52).

In the failing myocardium, metabolic disturbances are paralleled by a shift from fatty acid towards glucose oxidation. This effect results in reduced efficiency of energy generation in the myocardium, which in turn may contribute to the loss of contractile function in CHF. In an aging rat model the improvement of CHF by physical training is paralleled by a normalization of expression of PPARα in the myocardium.

Apart from their metabolic effects, little is known about the direct effects of PPAR activators on the heart. In isolated neonatal cardiomyocytes in vitro, both the PPARα activators fenofibrate and WY14,643 as well as the PPARγ activator rosiglitazone were able to prevent endothelin-1 induced hypertrophy. Similarly, the PPARγ activator reduced the hypertrophy induced by mechanical strain in isolated cardiomyocytes. In a model of arterial hypertension, PPARα and PPARγ activation were both able to reduce cardiac fibrosis. In a mouse model of acute myocardial ischemia and reperfusion, PPARα as well as PPARγ activation has been shown to reduce myocardial infarct size. In the chronic phase after myocardial infarction, PPARγ activators have shown to improve myocardial remodeling and heart failure symptoms (Liang et al. Endocrinology 2003, 144: 4187-4194). On the other hand, there is evidence that heart failure may be worsened by PPARγ agonists in patients with type 2 diabetes mellitus.

Thus, while the benefit of PPARγ activation in CHF is controversial, there are no data at all about the role of selective PPARα activation in CHF.

An embodiment of the present invention is the use of a compound of the formula (I)

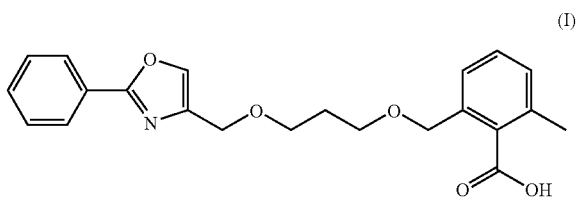

which may be identified as 2-methyl-6-[3-(2-phenyloxazol-4-ylmethoxy)propoxymethyl] benzoic acid, or a pharmaceutically acceptable salt or physiologically functional derivative thereof for the preparation of a medicament for the treatment of congestive heart failure (CHF).

A further embodiment is the use of a compound of the formula (II)

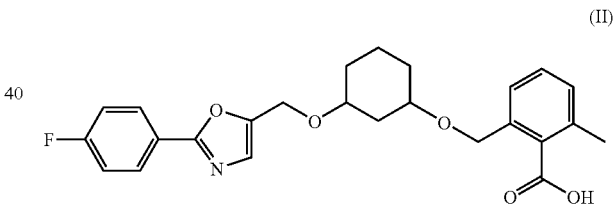

or a pharmaceutically acceptable salt or physiologically functional derivative thereof for the preparation of a medicament for the treatment of congestive heart failure (CHF).

A preferred compound of the formula (II) is the compound of the formula (III)

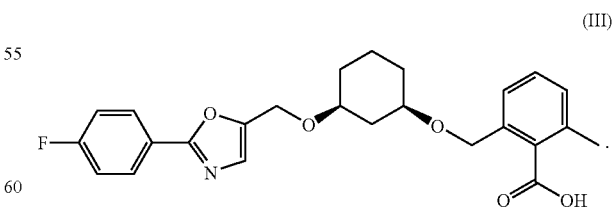

The compound of the formula (I) was prepared according to international patent application WO 2004/085377 (U.S. Pat. No. 6,989,462), example 5. Compounds (II) and (III) were prepared according to international patent application WO 03/020269 (U.S. Pat. No. 6,624,185), examples I and II.

Pharmaceutically acceptable salts are suitable for medical applications because of their greater solubility in water compared with the starting or base compounds. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts) and alkaline earth metal salts (such as magnesium and calcium salts).

The term "physiologically functional derivative" used herein refers to any physiologically tolerated derivative of a compound of formula (I) of the invention, for example, an ester which is able, on administration to a mammal such as, for example, a human, to form (directly or indirectly) a compound of formulae (I), (II) or (III) or an active metabolite thereof. Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves have activity or not.

The compounds of the invention may also-exist in various polymorphous forms, for example as amorphous and crystalline polymorphous forms. All polymorphous forms of the compounds of the invention belong within the scope of the invention and are a further aspect of the invention.

The amount of a compound of formula (I), (II) or (III) necessary to achieve the desired biological effect depends on a number of factors, for example the specific compound chosen, the intended use, the mode of administration and the clinical condition of the patient. The daily dose is generally in the range from about 0.3 mg to 100 mg (typically from about 3 mg to 50 mg) per day and per kilogram of body weight, for example about 3-10 mg/kg/day. An intravenous dose may be, for example, in the range from about 0.3 mg to 1.0 mg/kg, which can suitably be administered as an infusion of about 10 ng to 100 ng per kilogram and per minute. Suitable infusion solutions for these purposes may contain, for example, from about 0.1 ng to 10 mg, typically from about 1 ng to 10 mg, per milliliter. Single doses may contain, for example, from about 1 mg to 10 g of the active compound. Thus, ampoules for injections may contain, for example, from about 1 mg to 100 mg, and single-dose formulations that can be administered orally, such as, for example, capsules or tablets, may contain, for example, from about 1.0 to 1000 mg, typically from about 10 to 600 mg. For the therapy of the abovementioned conditions, the compounds of formula (I), (II) or (III) may be used as the compound itself but they may also be in the form of a pharmaceutical composition with an acceptable carrier. The carrier is acceptable in the sense that it is compatible with the other ingredients of the composition and is not harmful to the patient's health. The carrier may be a solid or a liquid or both and is often formulated with the compound as a single dose, for example as a tablet, which may contain from about 0.05% to 95% by weight of the active compound. Other pharmaceutically active substances may likewise be present, including other compounds of formula 1. The pharmaceutical compositions of the invention can be produced by one of the known pharmaceutical methods, which may essentially consist of mixing the ingredients with pharmacologically acceptable carriers and/or excipients.

Pharmaceutical compositions of the invention include those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula (I), (II) or (III) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, wafers, or tablets, each of which contain a defined amount of the compound of formula (I), (II) or (III); as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active compound and the carrier (which may consist of one or more additional ingredients) are brought into contact. The compositions are generally produced by uniform and homogeneous mixing of the active compound with a liquid and/or finely divided solid carrier, after which the product is shaped if necessary. Thus, a tablet can for example be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound which is in powder form and is moistened with an inert liquid diluent in a suitable machine.

Pharmaceutical compositions which are suitable for peroral (sublingual) administration comprise tablets that contain a compound of formula (I), (II) or (III) with a flavoring, normally sucrose and gum Arabic or tragacanth, and pastilles which comprise the compound in an inert base such as gelatin and glycerol or sucrose and gum Arabic.

The pharmaceutical compositions suitable for parenteral administration may comprise sterile aqueous preparations of a compound of formula (I), (II) or (III), which may be isotonic with the blood of the intended recipient. These preparations may be administered intravenously, although administration may also take place by subcutaneous, intramuscular or intradermal injection. These preparations can be produced by mixing the compound with water and making the resulting solution sterile and isotonic with blood. Injectable compositions of the invention generally contain from about 0.1 to 5% by weight of the active compound.

Pharmaceutical compositions suitable for rectal administration may be in the form of single-dose suppositories. These can be produced by mixing a compound of formula (I) with one or more conventional solid carriers, for example cocoa butter, and shaping the resulting mixture.

Pharmaceutical compositions suitable for topical use on the skin may be in the form of an ointment, cream, lotion, paste, spray, aerosol or oil. Suitable carriers are for example petrolatum, lanolin, polyethylene glycols, alcohols and combinations of two or more of these substances. The active compound is generally present in a concentration of from about 0.1 to 15% by weight of the composition, for example from about 0.5 to 2%.

Transdermal administration is also possible. Pharmaceutical compositions suitable for transdermal uses can be in the form of single plasters which are suitable for long-term close contact with the patient's epidermis. Such plasters suitably contain the active compound in an aqueous solution which is buffered where appropriate, dissolved and/or dispersed in an adhesive or dispersed in a polymer. A suitable active compound concentration is about 1% to 35% by weight, or about 3% to 15%. A possibility is for the active compound to be released by electro-transport or iontophoresis as described, for example, in Pharmaceutical Research, 2(6): 318 (1986).

In order to test the effect of specific activation of either PPARγ (rosiglitazone) or PPARα (compound of formula (I), (II) and (III)) on the improvement of CHF, a rat model of chronic coronary artery ligation was used because myocardial infarction is the most common cause for CHF in the industrialized countries.

It is shown herein that activation of PPARα is beneficial in congestive heart failure. With regard to myocardial function, both systolic and diastolic LV function—and therefore cardiac output—are improved after treatment with a compound of the formula (I), (II) or (III) but not with the PPARγ activator.

Activation of PPARα also improved pulmonary congestion, as evidenced by the normalization of both right ventricular and lung weight (a lower lung weight is an indicator for better heart function; a high lung weight indicates pulmonary congestion, which is frequently due to depressed function of the heart (i.e., CHF).

In previous studies, both PPARα and PPARγ activation had been reported to decrease myocyte hypertrophy in vitro, reduce fibrosis in mineralocorticoid dependent hypertension, and limit myocardial infarct size in acute ischemia-reperfusion models (vide supra). The opposing effects of activation of these two PPAR subtypes in post myocardial infarction heart failure were therefore unexpected. One of the reasons for the discrepant findings could be tissue specific differential expression of the two PPAR subtypes.

Abbreviations and Acronyms:
CHF=congestive heart failure
LV=left ventricle/ventricular
MI=myocardial infarction
PPAR=peroxisome proliferator activator receptor
SEM=Standard error of the mean

EXAMPLE 1

Proof of Concept Study for Use of a Compound of the Formula (I) for the Treatment of Congestive Heart Failure Male Wistar rats were housed three per cage under standardized conditions of temperature, humidity, and light. They had free access to a standardized diet (sodium content 0.2%, Altromin, Lage, Germany) and tap drinking water. Chronic heart failure was induced by a permanent occlusion of the left coronary artery approximately 2 mm distal to its origin from the aorta resulting in a large infarction of the free left ventricular wall. Chronic treatment was initiated on the day after production of the myocardial infarction and continued for eight weeks.

At the end of the treatment period, cardiac function was measured using an isolated working heart preparation (modified Langendorff apparatus, cf. Linz et al., J. Ren. Angiotensin Aldosterone Syst., 2003): The hearts were perfused according to Langendorff's method with an oxygenated (95% $O_2$, 5% $CO_2$) noncirculating Krebs-Henseleit solution of the following compositions (mmol/L): NaCl, 118; KCl, 4.7; $CaCl_2$, 2.5; $MgSO_4$, 1.6; $NaHCO_3$, 24.9; $KH_2PO_4$, 1.2; glucose, 5.5; Na-pyruvate, 2.0. The left atrium was cannulated by an incision of the left auricle. After a 15-minute equilibration period at a fixed perfusion pressure of 60 mmHg, the heart was switched into the working mode at a fixed filling pressure of 11 mm Hg. Then, afterload pressure was varied stepwise every two minutes from 40 to 140 mmHg. Data in the table are representative and given for a constant afterload pressure of 80 mmHg. Flow and pressure signals were sampled at 500 Hz, averaged every 2 seconds. Cardiac output measures the overall capacity of the heart to pump the blood through the body. LV dP/dtmax is an index of myocardial contractility, i.e. the force generating ability of the heart; LV dP/dtmin is an index of the ability of the myocardium to relax. In addition, lung weight was measured as an index of pulmonary congestion, an indirect sign of CHF.

Treatment with a compound of the formula (I) (pressed in chow, resulting in a dose of 20 mg/kg/d) was initiated on the day after myocardial infarction. The pure PPARγ agonist rosiglitazone was used for comparison in an additional group (3 mg/kg/day in chow).

Chronic treatment with the PPARα activator of the formula (I) improves different aspects of heart failure, whereas activation of PPARγ (using rosiglitazone) does not. Together, these data provide a strong rationale for a beneficial effect of a compound of the formula (I) in the treatment of congestive heart failure.

TABLE 1

| Test conditions | Lung weight Gram | Cardiac output mL/min | LV dP/dtmax mmHg/s | LV dP/dtmin mmHg/s |
| --- | --- | --- | --- | --- |
| Sham (No MI, no treatment) | 1.88 ± 0.10* | 37.3 ± 3.5* | 5780 ± 191* | 3527 ± 217* |
| MI Placebo | 2.96 ± 0.40 | 18.9 ± 2.9 | 3748 ± 176 | 2119 ± 75 |
| MI Rosiglitazone 3 mg/kg/d | 3.67 ± 0.38* | 10.2 ± 3.8* | 3491 ± 147 | 2081 ± 65 |
| MI compound (I) 20 mg/kg/d | 1.62 ± 0.06* | 25.8 ± 4.3* | 4614 ± 253* | 2502 ± 77* |

Data are mean ± sem. N = 6-12 per group.
*p < 0.05 vs. Placebo. Cardiac output, LV dP/dtmax and LV dP/dtmin were measured at an afterload of 80 mmHg (working heart).

EXAMPLE 2

Dose Response in Chronic Myocardial Infarction

Male Sprague Dawley rats were pre-treated with a chronic ligation of the left coronary artery, in order to produce a myocardial infarction (MI) and subsequent development of heart failure: Treatment with a compound of the formula (I) (pressed in chow, resulting in different daily doses) was initiated on the day after myocardial infarction. After 8 weeks of treatment, the animals were killed, the lung was weighed, and the function of the isolated heart was analyzed ex vivo in the working heart mode, in the same manner as described for Example 1 (vide supra). This method allows to assess different aspects of the myocardial function. For comparison against the effect of an established therapeutic principle in the present experimental series, the dual ACE/NEP, or vasopeptidase, inhibitor (7-(2-Acetylsulfanyl-3-methyl-butyrylamino)-6-oxo-1,2,3,4,6,7,8,12b-octahydro-benzo[c]pyrido[1,2-a]azepine-4-carboxylic acid; international patent application no. WO 02/083671) that is known for being active in the treatment of CHF was applied in an additional group.

Chronic treatment with a compound of formula (I) improves different aspects of heart failure. Together, these data prove a beneficial effect of the compound of the formula (I) in congestive heart failure.

L-glutamine (Life Technologies). Cultivation was carried out in standard cell culture bottles (Becton Dickinson) in a cell culture incubator at 37° C. and 5% $CO_2$. The 80% confluent cells were washed once with 30 ml of PBS (Life Technologies), treated with 2 ml of trypsin solution (Life Technologies) at 37° C. for 2 min, taken up in 5 ml of the medium described above and counted in a cell counter. After dilution to 500,000 cells/ml, in each case 100,000 cells were sown into each well of a 96-well microtiter plate having a clear plastic bottom (Corning Costar). The plates were incubated in a cell incubator at 37° C. and 5% $CO_2$ for 24 h.

Day 2: The PPARα agonists to be tested were dissolved in DMSO at a concentration of 10 mM. This stock solution was diluted in Phenol-Red-free DMEM medium (Life Technologies) to which 5% of cs-FCS (Hyclone), 2 mM of L-glutamine (Life Technologies) and the antibiotics described above (zeozin, G418, penicillin and streptomycin) were added. Test substances were usually tested at 11 different concentrations (10 µM; 3.3 µM; 1 µM; 0.33 µM; 0.1 µM; 0.033 µM; 0.01 µM; 0.0033 µM; 0.001 µM; 0.00033 µM and 0.0001 µM). More potent compounds were tested in concentration ranges of from 1 µM to 10 µM or 100 nM to 1 µM. From each well, the medium of the PPARα reporter cell line sown on day 1 was completely removed by aspiration, and immediately, the test substances diluted in medium were

TABLE 2

| Test conditions | Lung weight g/100 g BW | Cardiac output mL/min | LV dP/dtmax Mm Hg/s | LV dP/dtmin mm Hg/s |
|---|---|---|---|---|
| Sham (No MI, no treatment) | 0.39 ± 0.01* | 36.0 ± 2.7* | 5807 ± 192* | 2985 ± 109* |
| MI Placebo | 0.71 ± 0.07 | 7.3 ± 1.8 | 3170 ± 247 | 2056 ± 138 |
| MI compound (I) 1 mg/kg/d | 0.80 ± 0.08 | 12.5 ± 3.3 | 3280 ± 250 | 1886 ± 137 |
| MI compound (I) 3 mg/kg/d | 0.54 ± 0.08* | 21.5 ± 5.4* | 3665 ± 166* | 2353 ± 77* |
| MI compound (I) 10 mg/kg/d | 0.54 ± 0.09* | 21.0 ± 4.0* | 4043 ± 256* | 2339 ± 111* |
| MI VPI 30 mg/kg/d | 0.56 ± 0.07* | 27.2 ± 3.5* | 3868 ± 172* | 2379 ± 120* |

Data are mean ± sem. N = 6-12 per group.
*$p < 0.05$ vs. Placebo. Cardiac output, LV dP/dtmax and LV dP/dtmin were measured at an afterload of 80 mmHg (working heart).

EXAMPLE 3

Agonistic Efficacy of the Compound of Formula (I)

The agonistic activity of compounds of the formula (I) was tested according to WO 03/020269 as follows: To analyze the effectiveness of substances which bind to human PPARα, activating it in agonistic manner, a stable transfected HEK cell line (HEK=human embryo kidney) designated here as "PPARα reporter cell line" was used.

The activity of PPARα agonists was determined in a three-day test, described below:

Day 1: The PPARα reporter cell line was cultivated up to 80% confluence in DMEM medium (Life Technologies) with the following additives: 10% cs-FCS (foetal calf serum, Hyclone), antibiotics (0.5 mg/ml of zeozin [Invitrogen], 0.5 mg/ml of G418 [Life Technologies], 1% penicillin streptomycin solution [Life Technologies]) and 2 mM of added to the cells. Dilution and addition of the substances can be carried out using a robot (Beckman Biomek 2000). The end volume of the test substances diluted in medium was 100 µl per well of a 96-well plate. The DMSO concentration in the assay was always below 0.1% v/v to prevent cytotoxic effects of the solvent. To demonstrate that the assay was working in each individual plate, a standard PPARα agonist, which was also diluted to 11 different concentrations, was added to each plate. The test plates were incubated in an incubator at 37° C. and 5% $CO_2$ for 24 h.

Day 3: The PPARα receptor cells treated with the test substances were removed from the incubator and frozen at −20° C. for 1 h to improve cell lyses. After the plates had thawed (thawing at room temperature for at least 30 min), 50 µl of buffer 1 (Luc-Screen kit #LS1000, PE Biosystems Tropix) were pipetted into each well and the plates were then transferred into an apparatus for measuring luminescence, fitted with a pipetting unit (Luminoscan Ascent, Lab- Systems). The luciferase reaction in the measurement apparatus was started by pipetting 50 μl of buffer 2 (Luc-Screen kit #LS1000, PE Biosystems Tropix) into each well of the 96-well plate. Addition of buffer to the individual wells was carried out in defined and identical time intervals following the instructions of the manufacturer (LabSystems). All samples were measured exactly 16 min after addition of buffer 2. Measurement time is 10 sec per sample.

The PPARα agonistic activity of compounds (II) and (III), and the PPARγ agonistic activity of compounds (I), (II) and (III) can be determined in a similar manner.

The invention claimed is:

1. A method for the treatment of congestive heart failure (CHF) comprising the administration of a therapeutically effective amount of a compound of formula (I)

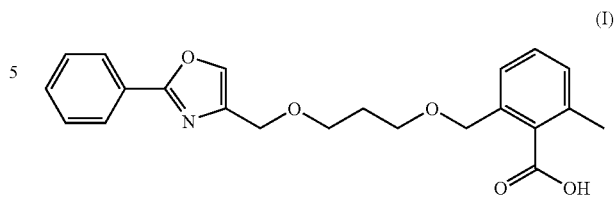

or a pharmaceutically acceptable salt thereof to a patient in need of such treatment.

* * * * *

UNITED STATES PATENT AND TRADEMARK OFFICE
CERTIFICATE OF CORRECTION

PATENT NO. : 7,601,863 B2  Page 1 of 1
APPLICATION NO. : 11/762799
DATED : October 13, 2009
INVENTOR(S) : Linz et al.

It is certified that error appears in the above-identified patent and that said Letters Patent is hereby corrected as shown below:

Please add to the Title Page of the Patent, after Item (65) "Prior Publication Data":

--Related U.S. Application Data

(63)   Continuation of application No. PCT/EP2005/013046, filed on Dec. 6, 2005.--

Signed and Sealed this

Sixth Day of April, 2010

David J. Kappos
*Director of the United States Patent and Trademark Office*